(12) United States Patent
Mihara

(10) Patent No.: US 9,364,138 B2
(45) Date of Patent: Jun. 14, 2016

(54) FREELY-ROTATING MINIMALLY-INVASIVE MEDICAL TOOL

(71) Applicant: Empire Technology Development LLC, Wilmington, DE (US)

(72) Inventor: Masaaki Mihara, Chiba (JP)

(73) Assignee: Empire Technology Development LLC, Wilmington, DE (US)

( * ) Notice: Subject to any disclaimer, the term of this patent is extended or adjusted under 35 U.S.C. 154(b) by 295 days.

(21) Appl. No.: 14/115,030

(22) PCT Filed: Jul. 4, 2013

(86) PCT No.: PCT/US2013/049408
§ 371 (c)(1),
(2) Date: Oct. 31, 2013

(87) PCT Pub. No.: WO2015/002655
PCT Pub. Date: Jan. 8, 2015

(65) Prior Publication Data
US 2015/0012021 A1 Jan. 8, 2015

(51) Int. Cl.
*A61B 17/00* (2006.01)
*A61B 1/018* (2006.01)
*A61B 17/29* (2006.01)

(52) U.S. Cl.
CPC ............... *A61B 1/018* (2013.01); *A61B 17/29* (2013.01); *A61B 2017/2929* (2013.01); *A61B 2017/2937* (2013.01)

(58) Field of Classification Search
CPC ............ A61B 10/06; A61B 10/04; A61B 2010/0208; A61B 17/28; A61B 17/29; A61B 2017/2905; A61B 2017/2908; A61B 2017/2903; A61B 2017/2913; A61B 2017/2915; A61B 2017/2916; A61B 2017/2933; A61B 2017/2934; A61B 2017/2936
See application file for complete search history.

(56) References Cited

U.S. PATENT DOCUMENTS

| 6,110,127 A | 8/2000 | Suzuki |
| 7,871,422 B2 | 1/2011 | Shibata |
| 2002/0087049 A1 | 7/2002 | Brock et al. |
| 2008/0132762 A1 | 6/2008 | Melville |
| 2009/0024141 A1 | 1/2009 | Stahler et al. |
| 2010/0030238 A1 | 2/2010 | Viola et al. |

FOREIGN PATENT DOCUMENTS

EP 1862107 A1 12/2007

OTHER PUBLICATIONS

Int'l Search Report, PCT/US12/49408, mailed Oct. 18, 2013, 12 pages.

*Primary Examiner* — Jonathan W Miles
(74) *Attorney, Agent, or Firm* — The Juhasz Law Firm P.C.

(57) ABSTRACT

The disclosure concerns a minimally-invasive medical instrument with a rotatable inner shaft mounting a medical tool. The medical tool may be, for example, a forceps, a grasper, a cutter or other medical tool useful for therapeutic or diagnostic procedures. The medical tool is desirably used in endoscopic, laparoscopic or other minimally-invasive procedures. The jaws or other end-effectors of the tool are operated by a first control wire, which will act to open or close the jaws or other end-effectors of the tool. A second control wire is used with a camming mechanism to transform linear movement of the second control wire into rotary motion of the inner shaft, thus also rotating the medical tool. The medical tool may thus be oriented at the surgical sit as desired by the surgeon, by rotating the tool without having to remove and re-place the tool within the patient.

36 Claims, 5 Drawing Sheets

FREELY-ROTATING MINIMALLY-INVASIVE MEDICAL TOOL

CROSS-REFERENCE TO RELATED APPLICATION

The present application is a U.S. national stage filing under 35 U.S.C. §371 of International Application No. PCT/US2013/049408, filed on Jul. 4, 2013.

TECHNICAL FIELD

The technical field of the disclosure relates to endoscopic medical devices.

BACKGROUND

Minimally-invasive medical procedures have become quite common over the past twenty or thirty years. Such procedures allow entry to a surgical site within the patient's body by endoscopic or laparoscopic means. An endoscope is a device that allows surgeons to perform minimally-invasive surgical procedures via a natural body opening, such as a throat or a urethra, to access the surgical site. In laparoscopic procedures, a small incision in made in the patient, in order to allow access to the abdomen or other site in the patient. After access is gained, medical devices may then use a natural body pathway, such as a vascular, renal or biliary pathway, to access the surgical site. Using minimally-invasive procedures helps avoid trauma to the patient by minimizing the pathway used to access the surgical site.

Once the surgeon and one or more medical tools have reached the surgical site, the procedure may begin. Often, however, the medical tool, such as a forceps or a grasper, is not precisely placed in order to perform its function. The surgeon may thus need to remove the medical tool from the site and re-introduce the tool so that it is properly placed and oriented in order to cut, grasp or otherwise perform its function. This may require several iterations, prolonging the operation and adding to the discomfort of the patient. These iterations should be minimized.

Unless otherwise indicated herein, the materials described in this section are not prior art to the claims in this application and are not admitted to be prior art by inclusion in this section.

SUMMARY

Technologies are herein described for a medical instrument that is useful in endoscopic and laparoscopic procedures, although these instruments are not limited to such use. An endoscope is introduced into the body of a patient through a natural body pathway, such as a throat or a urethra of the patient. Alternatively, the surgical site may be accessed by way of a small incision in the patient. Lumens or pathways in the endoscope then allow the introduction of medical tools, such as forceps or graspers. The medical tools described herein are rotatable about a longitudinal axis of the medical device. This allows the surgeon or medical professional greater freedom of movement of the medical device, and the surgeon thus has greater freedom in operating on the patient. For example, a biopsy forceps may be rotated in order to more easily approach a tissue sample for removal. Other medical tools may also be used in these procedures.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1A:
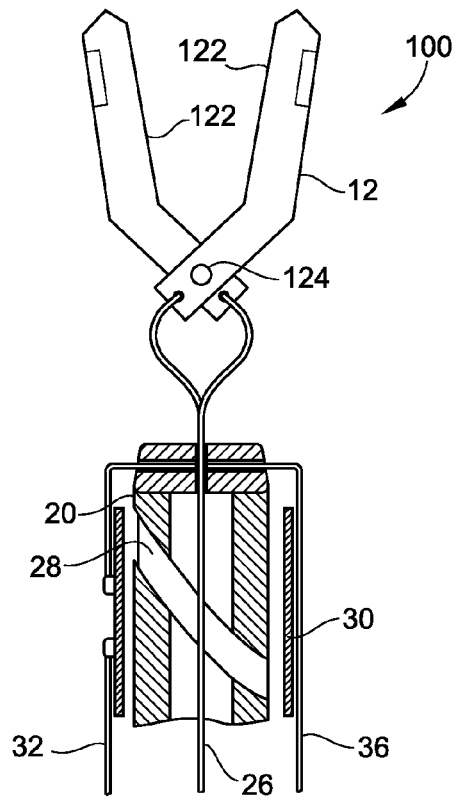
FIG. 1A is a simplified view of an embodiment of a medical instrument with a rotatable forceps.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Technologies are generally described for medical instruments or devices with a controllable medical tool on the distal end thereof. In the present context, the words distal and proximal are used in their ordinary and normal meanings. Distal is used to describe objects further from the surgeon or in a direction away from the surgeon. Proximal is used to describe objects nearer to the surgeon or in a direction toward the surgeon. The present disclosure includes improved devices and methods for controlling and maneuvering these medical tools. These medical tools are known in the prior art and are typically used to treat patients in a minimally-invasive manner. Entry of the tool into the patient is accomplished in a minimally-invasive manner using a natural pathway in the body, such as a throat or a urethra. Alternatively, access may be gained laparoscopically with a small incision, with specific access gained using a natural pathway within the body, such as a blood vessel, i.e. through vascular access. In this manner, trauma to the patient is minimized, risks of infection are kept low, and recovery time for the patient is much faster than in traditional, openly invasive procedures.

Minimally-invasive procedures are frequently accomplished with an endoscope, and medical instruments used with endoscopes may be termed endoscopic tools. The endoscope helps provide the pathway to the area of interest, and also may be equipped with additional facilities, such as an optical fiber for visual feedback to the surgeon or surgical team and illumination for the surgical site. The medical tools described herein are not limited to endoscopic procedures. For instance, access may also be gained by making a small incision and using an access sheath, the access sheath providing a pathway to the surgical site.

Previous forceps have been made using a flexible inner shaft within a flexible outer shaft. The inner shaft may be made of helically-wound wires, and thus remains flexible. The medical tool for which rotation is desired is mounted to the flexible inner shaft. The outer shaft may also have been made from a flexible wire or wires, or may have been made from a plurality of interlocking segments, the resulting outer shaft thus being flexible. The surgeon attempted rotation by physically rotating the proximal end of the flexible inner shaft. Alternatively, there may have been a control wire extending to the medical tool. As is well known in the art, however, it is typically necessary to maneuver the medical instrument by bending and turning the instrument along the length of the outer and inner shafts to reach the surgical site.

This is frequently accomplished using an endoscope, discussed above. The bends and turns along the way, even with an endoscope, cause significant friction when the surgeon attempts to rotate the medical tool. The friction causes binding between the inner and outer shafts until the frictional forces are overcome by the force applied by the surgeon. It was frequently possible, therefore, that instead of a gentle, controlled rotation, force was applied until the binding was overcome, resulting in a sudden and unexpected rotation of the medical tool. Thus, the movement of the forceps did not match the movement that was desired by the surgeon. Some prior art devices used a control wire that extended through the outer shaft to the medical tool. When rotation was desired, the control wire, wound around the medical tool, was pulled in order to cause rotation of the medical tool. Binding also applied in this situation. Prior art minimally-invasive surgical tools were difficult to handle and may have been useful only to very experienced physicians.

In describing this disclosure more fully, we make reference to the accompanying drawings, in which illustrative embodiments of the present disclosure are shown. This disclosure may, however, be embodied in a variety of different forms and should not be construed as so limited by the drawings. FIG. 1A depicts a front partial cross-sectional view of a first embodiment of an endoscopic medical instrument 100. The medical instrument 100 includes a medical tool 12 at a distal end of the medical instrument 100. In this embodiment, medical tool 12 is a forceps with forceps jaws 122. The forceps jaws are joined with an axle 124 that acts as a pivot point for the jaws. The axle is mounted atop an inner shaft 20. Opening and closing of the jaws is controlled by control wire or rod 26.

The inner shaft 20 and the medical tool 12 may be rotated by raising or lowering a sliding jacket 30 in contact with the inner shaft 20. Sliding jacket 30 includes wires 32, 36 for raising and lowering the sliding jacket. Sliding jacket 30 also includes a guide pin on its inner surface (not shown in FIG. 1A) that rides in a groove 28 in the outer surface of the inner shaft 20. The groove may be helical, so that as one wire 32 or the other wire 36 is pulled, the sliding jacket moves up or down with respect to the inner shaft. As the sliding jacket moves up or down, the inner shaft, and thus the forceps, rotates without advancing in an axial direction, i.e., the forceps rotates but does not move forward distally or backwards, that is, up or down as shown in FIG. 1A.

An outer shaft (not shown in FIG. 1A) surrounding part or all of inner shaft 20 provides a control handle for the user. The forceps may be used to excise material, such as a biopsy sample, for diagnostic purposes. Alternatively, the forceps or another medical tool may be used to excise material that should be removed from the body, and thus the forceps may be used for therapeutic purposes.

In operation, the surgeon, illustratively with one hand holding the outer shaft control handle, is able to rotate the inner shaft 20 and thus the forceps 12 that are mounted on the shaft by manipulating control wires 32, 36. This allows the surgeon to orient the forceps to the desire tissue, e.g., for incision or capture, which is accomplished using a second control wire. The surgeon opens and closes the jaws of the forceps to perform the forceps operation using control wire 26. Allowing the surgeon to rotate the forceps using control wires 32, 36 make it easier for the surgeon to orient the tool for the forceps operation so that the desired procedure may be efficiently carried out. The surgeon is able to spend less time and effort properly orienting the tool and more time carrying out the procedure.

Having thus introduced background on minimally invasive medical instruments, we now turn to features that are provided by this disclosure.

Technologies are generally described herein for rotatable medical tools that are useful in minimally-invasive procedures. The rotatable feature of the tool allows the surgeon to re-orient the tool without having to remove the device from the patient and then to re-insert the device and the tool. Thus, the medical tool can be quickly re-oriented in a desired manner by the surgeon. In many situations, the medical tool may be used within delicate tissues of the body, such as within vascular or blood vessels, i.e., within a vein or an artery of the patient, or within a ureter or a bile duct. If the medical tool must be inserted and withdrawn multiple times, each entrance and exit of the tool has potential for at least abrading tissue, with additional possibilities for scarring or perforating the tissue. If the tool can be correctly positioned by a small rotation, this eliminates at least a single additional exit and entry of the medical device with its tool.

Figure 1B:
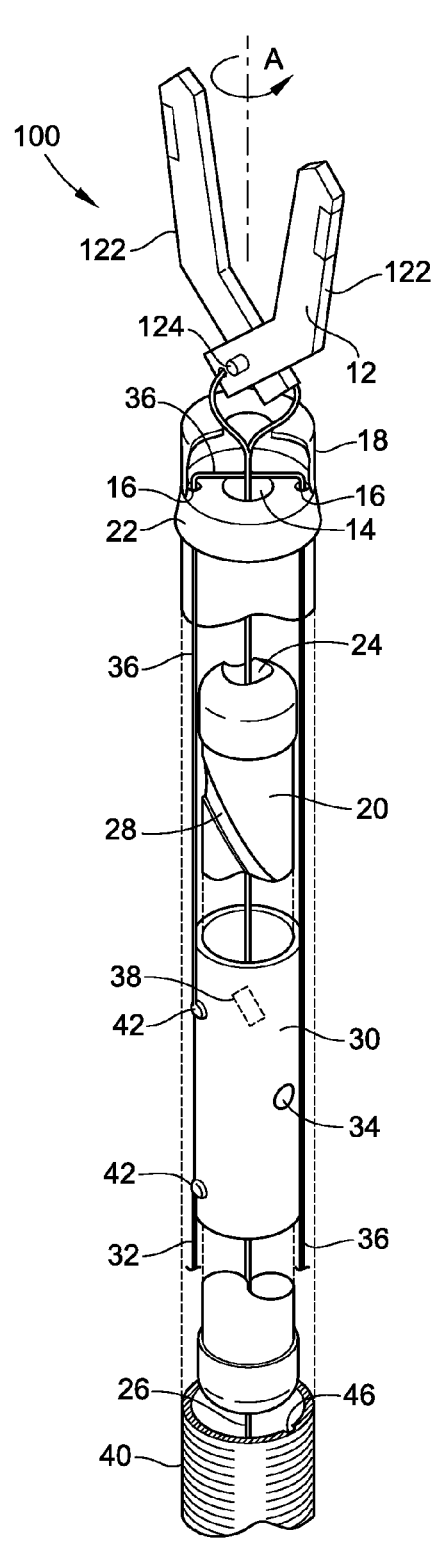
FIG. 1B is an exploded view of a portion of a medical instrument with a rotatable forceps according to this disclosure.
Figure 2:
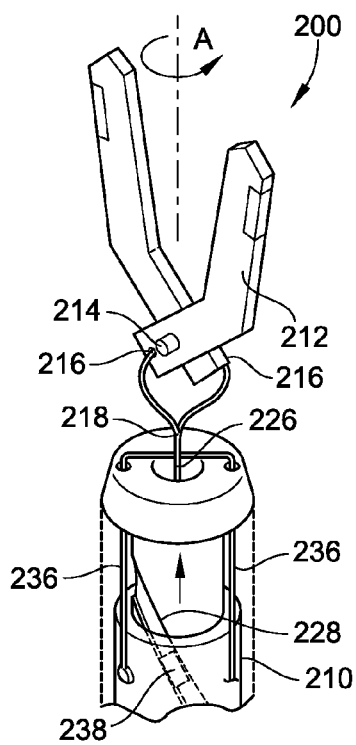
FIG. 2 is a close-up perspective view illustrating the rotatable forceps of FIG. 2 according to this disclosure.

Referring to FIGS. 1B and 2, the medical instrument 100 was previously described as including a medical tool 12 at a distal end of the medical instrument 100. In this embodiment, medical tool 12 is a forceps with forceps jaws 122. The forceps jaws are joined with an axle 124 that acts as a pivot pin for the jaws. The axle is mounted within mount 18. Although not shown, the mount 18 is configured to anchor the medical tool to the distal end of the shaft, with the lumen and control wires providing the manner in which to manipulate the medical tool according to this disclosure. Mount 18 may be secured to the cap via snap fit, brazing, or any other process which is medically acceptable. Inner Shaft 20 is provided with a mounting cap 22 and a lumen or opening 24 for a first control wire 26, which is attached to the forceps, for controlling the opening and closing of the forceps.

Mounting cap 22 includes a central orifice 14 for the first control wire 26, and also includes two additional orifices 16 for passage of a second control wire 36. Second control wire, with two portions 32, 36 extends from the mounting cap down along the outside of the inner shaft 20 on two sides of the inner shaft. Second control wire 32, 36 is fastened to a sliding jacket 30, which fits between inner shaft 20 and the forceps flexible outer shaft 40. The control wire 32, 36 may be fastened with welding beads 42, alternatively, the control wire may instead be brazed to the sliding jacket, or adhered in any reliable and medically acceptable manner. The control wire may be two wires 32, 26 as depicted in FIGS. 1A and 1B, or may be a single wire adhered, welded, soldered or brazed as desired. Control wire 32, 36 allows rotation of the medical tool in a manner that is described below.

The interaction between the inner shaft 20, sliding jacket 30 and flexible outer shaft 40 allows the surgeon or other medical professional to rotate the medical tool 12 along a longitudinal axis A as herein described. Sliding jacket 30 includes an outer guide pin 34 for riding in a longitudinal slot 46 of the flexible outer shaft 40. This outer guide pin 34 prevents rotation of the sliding jacket 30 with respect to the flexible outer shaft 40 and maintains rotary alignment between the jacket and the shaft while allowing linear or translational movement of the sliding jacket with respect to the flexible outer shaft.

The sliding jacket 30 also includes an inner guide pin 38 that fits into an outer groove 28 on the inner shaft 20. Groove 28 may be a helical or spiral groove or may have any shape or orientation that is useful in allowing the surgeon to rotate the medical device. As noted above, the second control wire 32, 36 is attached to the sliding jacket 30. When the left portion 32 of the second control wire is pulled downward, the sliding jacket 30 is also pulled downward. Outer guide pin 34 of sliding jacket 30 travels in longitudinal slot 46 on the inner side of flexible outer shaft 40 and thus maintains the alignment of the sliding jacket 30 with respect to the flexible outer shaft 40. When control wire 32 is pulled downward, sliding jacket 30 is also pulled downward but cannot rotate because rotation is prevented by outer guide pin 34 riding in slot 46. As the sliding jacket 30 is pulled downward, inner guide pin 38 travels in groove 28 and forces clockwise rotation of flexible inner shaft 20. Thus, a downward pull of control wire 32 will result in a clockwise rotation of the inner shaft 20.

In the same manner, if the other portion 36 of the control wire is pulled downward, sliding jacket 30 will instead be pulled upwards, forcing counter-clockwise rotation of flexible inner shaft 20. Using this technique, the surgeon is able to rotate the inner shaft 20 and thus the forceps 12 that are mounted on the shaft. This allows the surgeon to orient the forceps to the desire tissue, e.g., for incision or capture. Allowing the surgeon to rotate the forceps makes it easier for the surgeon to orient the tool so that the desired procedure may be efficiently carried out. The surgeon is able to spend less time and effort properly orienting the tool and more time carrying out the procedure.

A closer view of the rotatable medical tool 200 is depicted in FIG. 2. In this view, the cap and the second control wire are not shown, for greater clarity. The rotatable medical tool includes forceps 212, including two forceps jaws as shown, joined at an axle 214 which acts as a pivot point for the forceps jaws. The opening and closing of the jaws is accomplished with wires fastened at proximal points 216 of the jaws, the wires then joined together at a juncture point 218 to form a single control wire 226. The forceps is mounted to the flexible inner shaft 210 via the cap (not shown in FIG. 2). Flexible inner shaft 210 includes a helical groove 228 which accommodates guide pin 238 from a sliding jacket (not shown).

As the sliding jacket and the guide pin 238 move upwards in FIG. 2, flexible inner shaft 210 will rotate counter-clockwise, as shown. It is also possible to orient the helical groove in the opposite direction, so that when the guide pin moves downwards, the shaft will rotate clockwise. Either orientation will work well.

Figure 3:
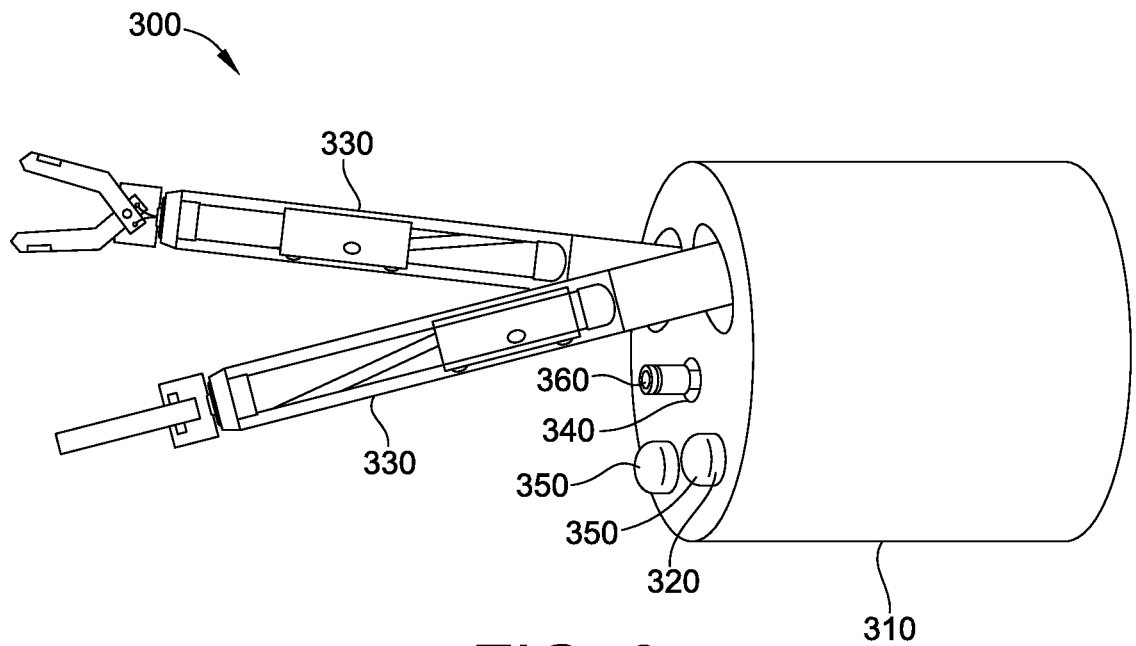
FIG. 3 is a perspective view of an endoscope utilizing the rotatable forceps of FIGS. 1 and 2.

Minimally-invasive tools are often used in conjunction with an endoscope, as shown in FIG. 3. In endoscopic surgery, an endoscope 310 may be introduced into a patient through a natural pathway into the patient's body. Endoscope 310 includes lumens 320 or paths that allow surgical instruments such as forceps 330 to be introduced to the surgical site. The endoscope also includes additional lumens 340 for illumination sources 350 and for a fiber optic viewing system 360. In this embodiment, two forceps 330 are shown to emphasize that multiple forceps may be used cooperatively. Because the rotatable forceps are so maneuverable, they may enable the surgeon to operate more than one forceps concurrently. The forceps can be operated by a single hand of the surgeon or member of the medical team attending the patient.

Figure 4:
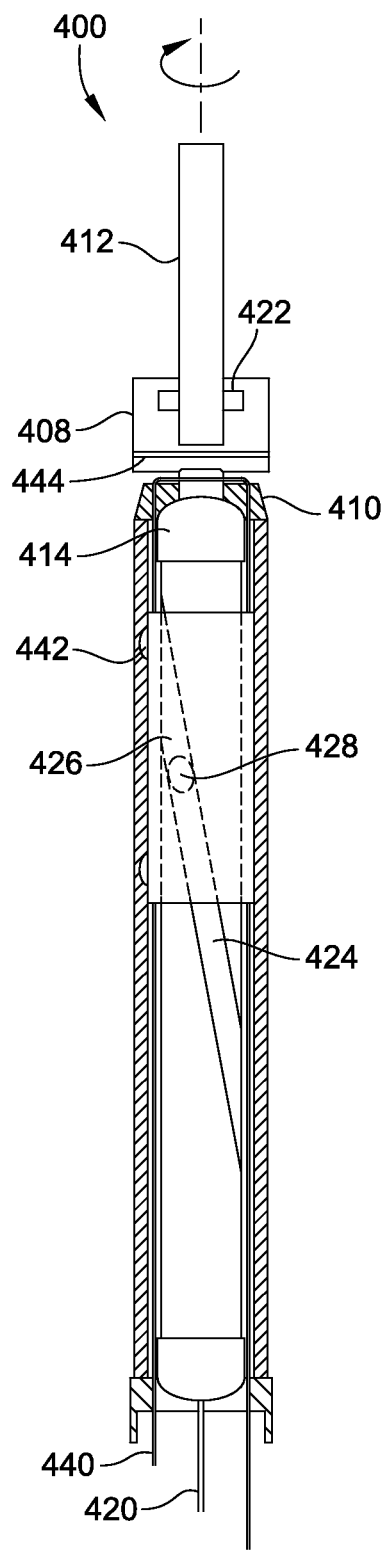
FIGS. 4 and 5 are perspective views illustrating use of a control wire to rotate the forceps or other medical tool atop the medical instrument.
Figure 5:
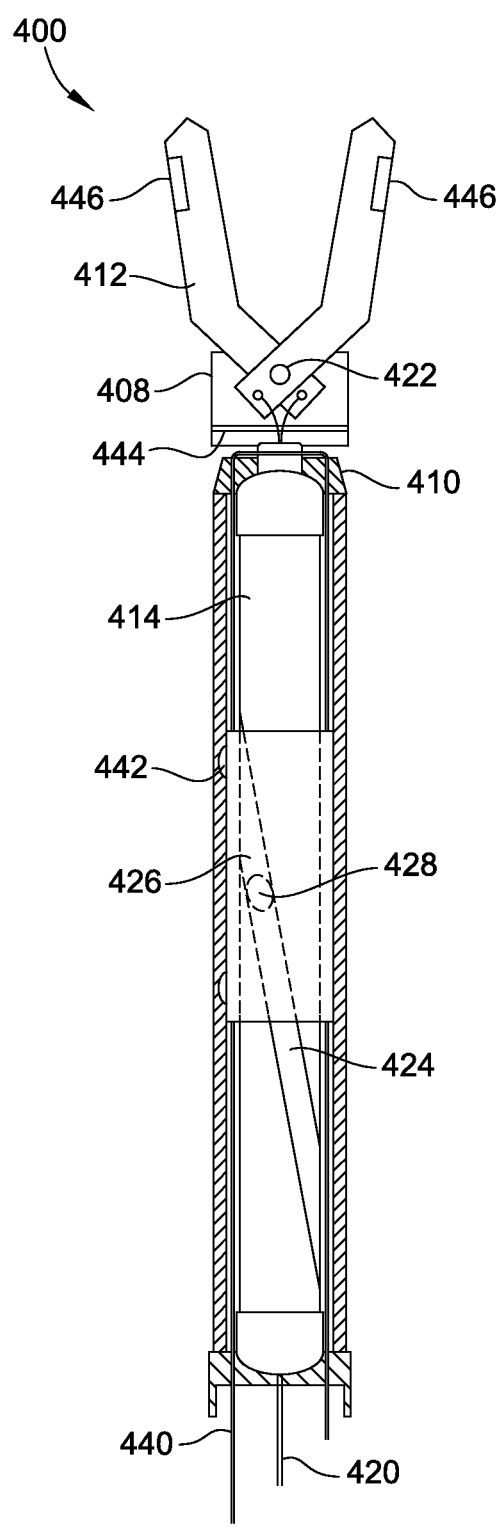

Additional details of the rotatable forceps are shown in FIGS. 4 and 5. In FIG. 4, the rotatable forceps 400 is in an initial position, as shown without the outer flexible shaft, so that inner details may be more visible. In FIG. 4, the forceps 412 is seen in profile, while in FIG. 5, the forceps has been rotated ninety degrees clockwise. The tool also includes the forceps base 408, forceps pivot pin or axle 422 fixedly mounted in forceps base 408, forceps mounting cap 410, flexible inner shaft 414, flexible inner shaft groove 424 and sliding jacket 426. The sliding jacket 426 includes an inner guide pin 428 that rides within groove 424. The controls for the forceps include first control wire 420, for controlling the opening and closing of the forceps. Second control wire 440 controls the movement of the sliding jacket 426 and is attached to the sliding jacket as shown, with attachment points 442 shown in exaggerated size for clarity.

When the surgeon wishes to maneuver the forceps backwards or forwards, the entire forceps instrument, including the outer shaft (not shown in FIGS. 4 and 5), is advanced or retreated, as would be the case with a forceps according to the prior art. When the surgeon or other user wishes to open or close the forceps jaws, the first control wire 420 is used. When the surgeon wishes to rotate the jaws of the forceps, to better orient the jaws with the tissues of the patient, second control wire 440 is used. In this example, the left-side portion of control wire 440 is pulled downward. Note the different lengths of control wire 440 as depicted in FIGS. 4 and 5. In FIG. 4, the left-side portion of control wire 440 is higher than the corresponding position of control wire 440 in FIG. 5, which is lower than in FIG. 4.

Since the left-side portion of control wire 440 was pulled downward, the sliding jacket 426 is also pulled downward. Note the difference in height of sliding jacket 426 between the views of FIGS. 4 and 5. When the sliding jacket 426 is pulled downwards on the left portion of the control wire 440, guide pin 428, riding in groove 424, forces inner shaft 414 to rotate, in this case in a clockwise manner, as depicted in FIG. 4. The orientation of groove 424 corresponds to a left-handed thread; a right handed thread will work as well.

Note that both portions of the control wire 440, the left portion and the right portion, work in tandem. Thus, if the user pulls on the left hand portion of the wire, as shown in FIG. 4, the left hand portion of the wire goes to a lower position, as shown in FIG. 5. With this same motion, the right hand portion of control wire 440, shown low in FIG. 4, is pulled up, as shown in FIG. 5. Control wire 440 is routed through forceps mounting cap 410 and as noted, the portions of the wire are connected at least through their connection to the sliding jacket 426. If the surgeon wishes to reverse the rotation, the opposite side of the control wire 440 is pulled. When the right side of the rotation control wire 440 is pulled, the sliding jacket rises, and the jaws of the forceps rotate in the opposite direction, i.e., counterclockwise. Thus, the mechanism allows the single rotation control wire to rotate the forceps clockwise or counter-clockwise, as desired.

Also seen in FIG. 5, forceps base 408 and forceps jaws 412 may include features 444, 446 for easy detection via non-intrusive detection equipment. Detection features 444, 446 may include radiopaque or echogenic features, which are well known in the art. The radiopaque features may be small pieces of metal that are highly visible when viewed with fluoroscopic or other visualization techniques. Metals for radiopaque markers may include gold, tantalum, iridium, and platinum, among others. Detection feature 444 may be a thin band of metal placed in a slot or a groove of the forceps base, as shown. Radiopaque features 446 may be placed on the forceps jaws as shown, placed as desired for best visibility by the surgeon.

Alternatively, echogenic features, well known in the prior art, may be used. Echogenic features are typically small dimpled areas which are highly reflective of ultrasonic radiation. Echogenic features may also include indentations, grooves or other similar features that allow for multiple reflections of ultrasonic waves. These features are highly visible when viewed with ultrasound equipment during a procedure. These features allow the surgeon to follow the progress of the medical tool as the surgeon advances the tool within the endoscope and within the patient.

The guide pin 428 and the groove 424 act as a camming mechanism, that is, they act as a device to transform linear motion into rotary motion, or vice versa. In this application, the linear motion of the second control wire is transformed into rotary motion of the inner flexible shaft. The inner flexible shaft mounts the forceps, and thus when the inner flexible shaft rotates, the forceps also rotates. The end result is that the camming mechanism formed by the guide pin and the groove transform linear motion of a control wire into rotary motion of the medical tool.

The angle of the helical groove with respect to the longitudinal axis determines the rate at which the travel of the control wire is turned into angular rotation of the medical tool. In one embodiment, the angle of the groove may be such that about one inch (about 2.5 cm) of control wire travel is sufficient to cause about ninety degrees of rotation of the medical tool. Without limitation, other transformational rates may also be used, e.g., about 1 cm of control wire travel may be sufficient to cause about ninety degrees of rotation. Other angles may be used as desired, varying the travel of the control wire that is required to rotate the medical tool a given angle. While a ninety-degree rotation is easily visualized, it may be that the surgeon requires a greater or a lesser amount of rotation of the medical tool. The only limit on the angle of rotation is the amount of control wire available in the control handle (described below) that controls the control wire movement.

The fit of the guide pin in the groove should be sufficiently tight that very little play is left. That is, once the surgeon has caused the control wire to move, and the tool to rotate, the tool should not be loose, i.e., there should be very little "play" in the rotational freedom of the device.

The minimally-invasive tools discussed herein are under the absolute control of the surgeon. Most movements tend to be extension or retraction of the device to or within the surgical site, with small side-to-side movements for placing the medical device and the end-mounted tool in the precise position desired by the surgeon. The radiopaque or echogenic features of the medical instrument or the medical tool may assist in the placement of the device, as discussed above, using non-invasive visualization techniques also discussed above.

Figure 6:
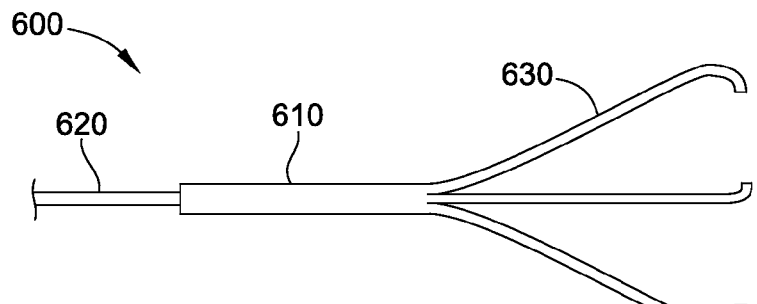
FIGS. 6 and 7 are perspective views of additional rotatable medical tools that may be used with the medical instrument according to this disclosure.

In addition to the forceps discussed above, other medical or surgical tools may also be desirably rotated during surgical procedures. As shown in FIG. 6, a three-pronged grasper 600 may also be used with the present disclosure. Three-pronged grasper 600 may include a central shaft 610, a first control rod or wire 620, and three prongs 630. The surgeon may control grasping of the grasper 600 by advancing or retracting the grasper when it has advanced to the proper site. Using the present disclosure, the grasper may be mounted, just as the forceps is mounted, in the manner depicted in FIGS. 4-5.

Figure 7:
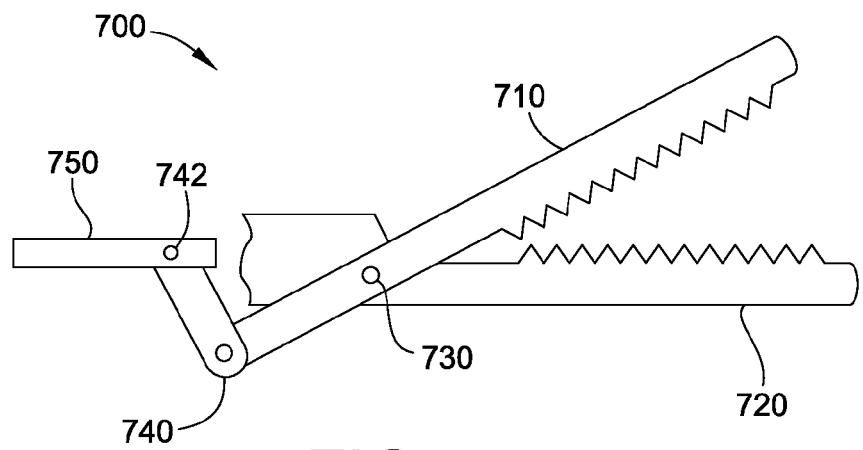

An additional alternate medical tool, a cutting tool 700, as shown in FIG. 7, may also be mounted for rotation as described herein. Cutting tool 700 includes a moveable jaw 710, a fixed jaw 720, and a pivot point 730 joining the jaws. Moveable jaw 710 is moved by a control wire 750 pulling on second and third pivot points 740, 742 to open or close the jaws. Other surgical tools or end-effectors may also be used. These include, without limitation, other grasping and retrieval devices, snares, cutters, and any other medical tools suitable for minimally invasive surgery.

Figure 8:
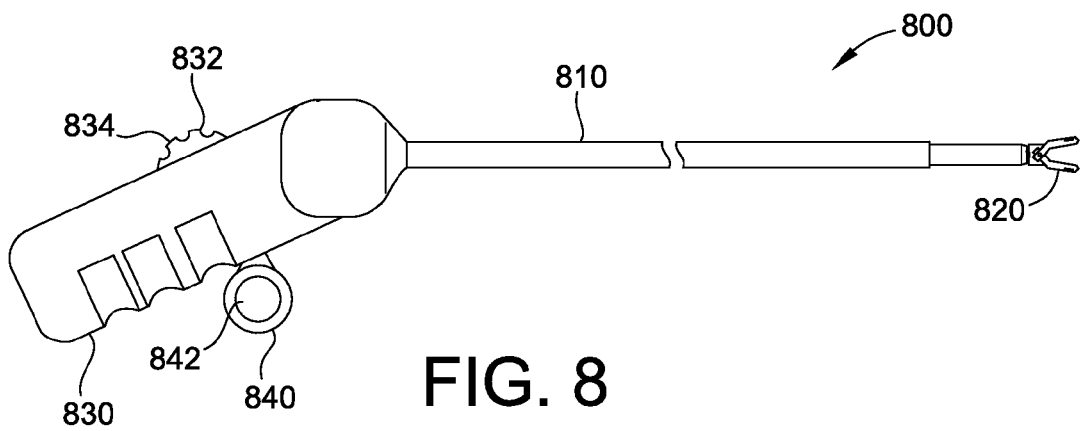
FIG. 8 is a perspective view illustrating an endoscopic medical device with a rotatable tool on a distal end of the endoscopic medical device.

The rotatable forceps, or other minimally-invasive surgical instrument is easily used with a control handle, as shown in FIG. 8. Endoscopic instrument 800 may include an endoscopic device 810 mounting an endoscopic tool or medical tool 820, and a control handle 830. Control handle 830 includes controls for opening and closing the endoscopic tool 820 mounted on the endoscopic device 810. In this embodiment, the controls include a thumbwheel 832, with teeth 834 for easy gripping, and a trigger 840, with a finger opening 842.

The operator or surgeon can open or close the medical tool by pulling or releasing the trigger 840. The surgeon can easily rotate the medical tool by advancing or retracting the thumbwheel, thus advancing or retracting the second control wire discussed above.

Figure 9:
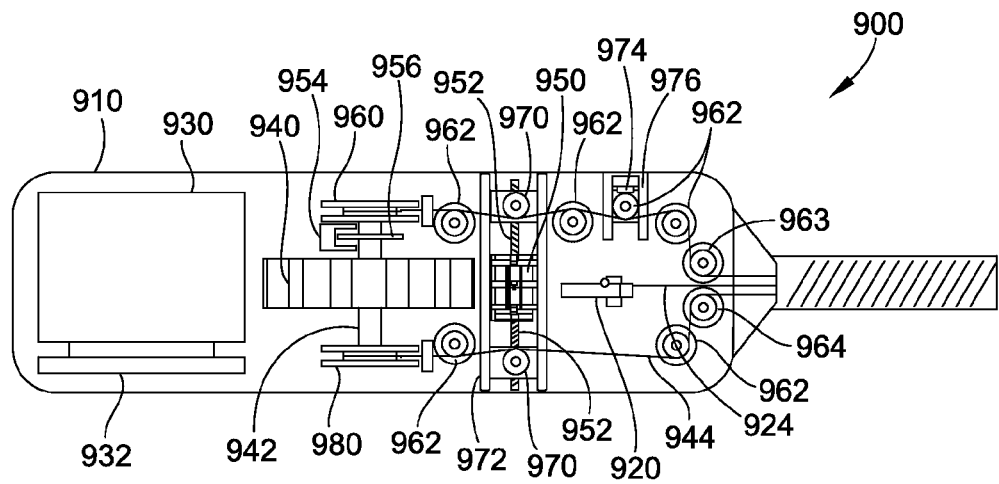
FIG. 9 is a plan view of a tension control mechanism for the wire controlling rotation of the medical tool.
Figure 10:
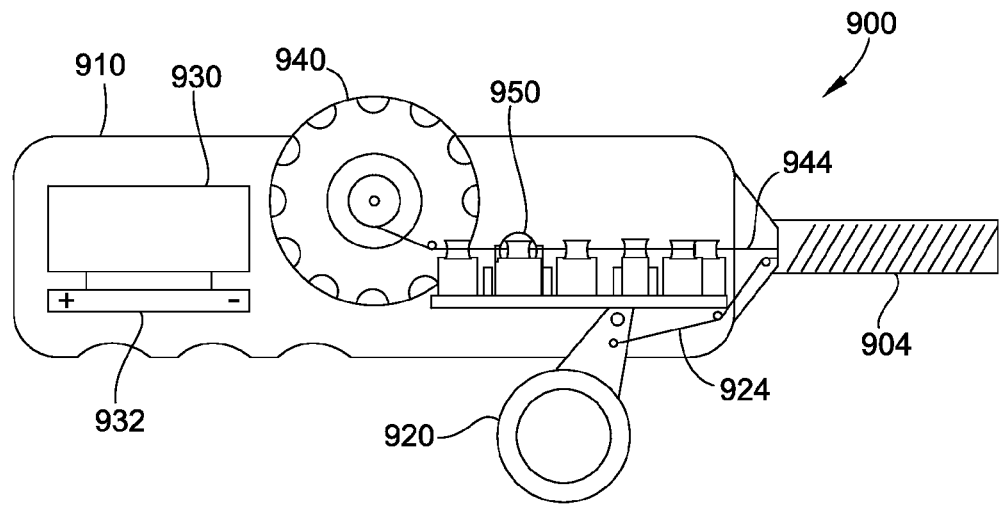
FIG. 10 is an elevational view of the tension control mechanism according to FIG. 9.

Further details of the controls for the second control wire are now discussed with reference to FIGS. 9 and 10. FIG. 9 is a top plan view of a handle and controller 900 for a medical device 904 and medical tool (not shown in FIGS. 9 and 10), according to the present disclosure. FIG. 10 is a side view of the same controller with the same components represented by the same images and numerals. A side-perspective view of the handle, medical device and medical tool is also provided in FIG. 8, showing the general appearance of this embodiment.

Controller 900 includes a handle 910, a control portion 930 and a power supply 932, such as a battery. The power supply is needed for the control portion 930 and for a small motor 950, which may be a stepper motor. Controller 900 is primarily, however, a manual device. That is, the handle 910 includes a trigger 920 for pulling or releasing first control wire 924. First control wire 924 is used in this embodiment to open or close a forceps or other medical device. The handle 910 also includes a thumbwheel 940 for advancing or retracting the second control wire 944. Second control wire 944, in this embodiment, corresponds to the control wire of FIGS. 4-5 that is used for rotation of the medical tool.

Thus, the handle and controller is primarily a manual controller. As described herein, the control portion 930 and a small motor 950, which may be a stepper motor, are primarily used to keep a light tension on the second control wire 944. A stepper motor is typically a small, brushless DC motor that divides each full rotation of its rotor or moving portion into an equal number of steps. The motor will rotate a small angle, typically a small portion of a full rotation, three-hundred and sixty degrees, for each "step" or actuation provided by a micro-controller that is controlling the motor. Thus, if the tension control stepper motor requires one hundred steps for a full rotation, each step will cause the tension-control stepper motor to rotate 3.6 degrees. This rotation relates only to the rotation of the motor as it keeps tension on the second control wire, and is not related to the rotation of the medical tool.

At least one advantage of the stepper motor is that no feedback is required, because the controller can "count" each step as it activates the motor and causes rotation. The pressure sensor will continuously provide tension feedback and thus keep tight control on the tension of the wire.

As discussed above, tension control is primarily maintained by the surgeon or other medical professional and the thumbwheel. The tension control device described here is primarily intended to compensate for stretching of the control wire 944. Keeping this tension on second control wire 944 insures that the wire is not slack. Thus, the rotation of the medical tool and its position always firmly controlled by the surgeon.

Control wire 944 is first wound onto wire feed or unwind roller 960, at the top of FIG. 9, and is taken up by rewind roller 980, at the bottom of FIG. 9, after the wire has traversed the path depicted in FIG. 9. Thumbwheel 940 is mounted on shaft 942, which also mounts wire unwind roller 960 and rewind roller 980. Wire 944 unwinds and is guided through a plurality of guide rollers 962 until wire 944 reaches rewind or takeup roller 980 at the end of its path through the handle. When wire 944 reaches guide roller 963, the wire travels into medical device 904 and is connected as shown previously, to a medical tool in order cause rotation of the medical tool. The wire then returns from the medical tool at guide roller 964. The wire then encounters additional guide rollers 962 until it reaches rewind or takeup roller 980.

Along its path, wire 944 receives tension control from tension rollers 970 on both sides of tension control motor 950. Tension control motor 950 and rollers 970 are fixedly mounted on shaft 952, which is not a rotating or moving shaft of motor 950. The motor 950 and rollers 970 may traverse back and forth within motor mount 972, e.g., through a traveling mechanism propelled by the motor. In this embodiment, the motor and the rollers 970 move forwards and backwards as an assembly, up and down as shown in FIG. 9. Tension is read by a pressure sensor 974 in pressure sensor mount 976. Tension is maintained by causing control portion 930 to activate the motor 950, in response to the reading of pressure sensor 974. The control portion 930, in response to the pressure reading, activates motor 950, causing the motor and rollers to move one way or the other with respect to the motor mount 972. Rotation in a first direction will cause the motor 950 and the tension control rollers 970 to move together, upwardly in their mount 972 in FIG. 9, to relieve a high tension reading of pressure sensor 974. Rotation of the motor in a second, opposite direction will cause the motor 950 and tension control rollers 970 to move downwardly in mount 972, placing additional tension on wire 944 until the pressure sensor 974 reads a sufficiently high pressure for the control portion 930 to cause rotation of motor 950 to cease, thus stopping movement of the motor and the tension control rollers 970.

Thumbwheel 940 is also equipped with a photo-interrupter 954 with optical slits 956, as shown in FIG. 9. The photo-interrupter 954 is in communication with control portion 930. When the surgeon or other medical professional rotates thumbwheel 940, the rotation may cause at least a momentary increase or decrease of tension in the wire 944, noted by pressure sensor 974. At that movement, however, it is more important that the surgeon maintain control of the medical tool than to take up any possible slack in the wire. Accordingly, in one embodiment, when the photo-interrupter detects movement through the optical slits, the control temporarily disables the motor and tension control is not resumed until the movement ceases. When the photo-interrupter subsequently detects no motion, the motor is re-enabled and normal tension control may be resumed.

Figure 11:
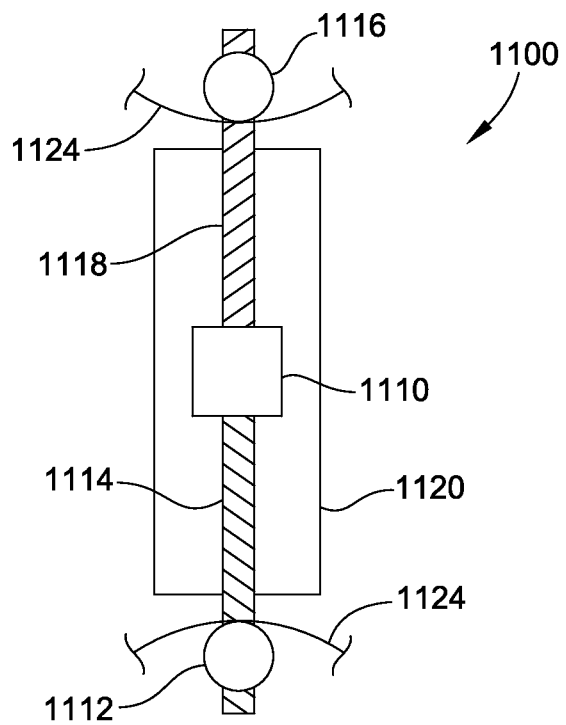
FIG. 11 is an alternate embodiment of the tension control mechanism according to FIG. 9; all of the figures arranged according to at least some embodiments presented herein.

An alternate embodiment of the tension control mechanism is disclosed in FIG. 11. In this embodiment, the motor 1110 is mounted fixedly in motor mount 1120 and does not move. The motor 1110 has two rotating shafts 1114, 1118 as shown. In this embodiment, lower spool 1112 is mounted on the take up side of the tension control mechanism, i.e., similar to the bottom portion of FIG. 9, with wire 1124 leading to the wire re-wind or take-up roller 980 (see FIG. 9). Lower spool 1112 is mounted on shaft 1114, which has left-handed threads. On the other side of this embodiment of the tension control mechanism, upper spool 1116 is mounted on shaft 1118, which has right-handed threads. At this point, wire 1124 is fed from wire unwind roller 960 (see FIG. 9). Spools 1112, 1116 may be placed on mounts in a track (not shown) for extra stability, as they traverse in and out, towards or away from the motor, when the motor activates to increase or decrease tension in the wire.

It is known in the prior art that a motor with this configuration may be used to simultaneously pull in objects on opposite sides of the shaft, or to push them out. An example is a motor used for wiper blades, in which it is desired to cause virtually the same motion on both sides of the motor, but in opposite directions. The portion between the oppositely-threaded portions of the shaft may have a reduced diameter so as to more readily permit manufacturing of a single shaft. Alternatively, the shafts may be formed as two portions and joined, e.g., by inner and outer threaded portions in the middle of the shaft. In this case, the shaft may have a central portion that forms the rotor of the motor itself, the central portion of the rotor shaft held within the stationary stator of the motor. Thus, the two oppositely-threaded shafts may be parts of a single shaft or may be two shafts joined to form a single shaft assembly.

Upper spool 1116 guides wire 1124 from the wire unwind roller 960 while lower spool 1112 guides the wire to the take-up spool. When the motor rotates in a first direction, the two shafts 1114, 1118 will both rotate in a first direction and will cause the spools to move inwardly, i.e., towards the motor, thus increasing tension on the wire. When the motor reverses direction, the shafts rotate in the opposite direction, the spools will move outwardly and will reduce tension on the wire.

As noted previously, the stepper motor is capable of very small increments of movement, so that the inward and outward movement of spools 1112, 1116 is controlled in very small increments, perhaps as fine as thousandths of an inch (0.001 inch is about 0.0254 mm). When the controller notes a decrease in tension, the controller will cause the motor to rotate in a first direction, moving the spools inwardly. The wire on both sides of spools 1112, 1116 is guided by other guide rollers 962. Pulling in spools 1112, 1116 will increase tension on the wire by increasing the path traversed by the wire between the un-wind and take-up spools. In contrast, when the tension is too high, the controller will activate the motor to rotate in the opposite direction, moving the spools outwardly and decreasing the length of the wire path between the un-wind and take-up spools. Thus, a very simple mechanism helps to maintain constant tension on the wire and helps the surgeon maintain precise control over the rotation of the tool on the end of the flexible inner shaft of the medical instrument.

In view of this disclosure, it will be seen that technologies are generally described for medical tools suitable for minimally-invasive procedures, such as endoscopic or laparoscopic procedures. A medical instrument that typically includes a flexible outer shaft and a flexible inner shaft, is equipped with a mechanism that allows a surgeon to rotate the flexible inner shaft with respect to the outer shaft. A medical tool, such as a grasper or a forceps, is mounted on the flexible inner shaft. The surgeon is thus able to rotate the medical tool by rotating the flexible inner shaft. This additional freedom of movement allows the surgeon to more easily maneuver the medical tool to the precise position desired in the surgical field. Thus, medical procedures may be more readily carried out at the surgical site. These may include taking a biopsy sample, excising tissue, grasping objects for retrieval, and so forth.

The advantages of the method and the devices useful in carrying out the method include mechanical simplicity. The mechanism that enables rotation of the inner shaft of the medical instrument also prevents rotation of the outer shaft, which may be in the grasp of the surgeon or contained in a control handle. This mechanism is a sliding jacket held between the inner and outer shafts and equipped with inner and outer guide pins. The outer guide pin is secured in a longitudinal groove on an inside of the outer shaft. The outer guide pin prevents rotation of the outer shaft with respect to the sliding jacket. The inner guide pin of the sliding jacket mounts within a helical groove on the outside of the inner shaft. The sliding jacket moves up or down by means of a control wire attached to the sliding jacket. The control wire is also mounted to a cap atop the flexible inner shaft, and control wire running through the cap and down both sides of the inner shaft.

When the surgeon wishes to rotate the medical tool atop the flexible inner shaft, the surgeon pulls the control wire one way or the other, causing the sliding jacket to slide up or down, guided by the guide pin mounted in the helical groove of the inner shaft. The guide pin bears against the walls of the groove. Since the outer shaft cannot rotate, the force of the guide pin causes rotation of the inner shaft. If the wire is pulled in a first direction, the guide pin causes clockwise rotation of the inner shaft and the medical tool mounted to the inner shaft. If the wire is pulled in the opposite direction, the guide pin causes counter-clockwise rotation of the inner shaft and the medical tool mounted to the inner shaft.

This ease of movement allows the surgeon a great deal of freedom to maneuver the medical tool in the surgical site. The surgeon is able to move the medical instrument and medical tool forwards and backwards, i.e., extending in a distal direction and retracting in a proximal direction. The surgeon is now able to also rotate the medical tool without first withdrawing the medical tool. If the medical instrument and medical tool are extended into a body cavity or body lumen of the patient, repeated introduction and withdrawal of the instrument may cause at least irritation to the tissues. Examples may include repeated introductions to a vein, a ureter or a urethra of a patient. If the surgeon may position a forceps or a grasper into a correct position for the procedure by merely rotating the forceps of the grasper, additional irritation to the patient, or even trauma to the body pathway or cavity, may be avoided. Repeated introductions and withdrawals of surgical instruments typically require more time than the rotations of the devices disclosed herein. Thus, the rotating medical tools may also allow procedures to be accomplished in less time than before.

The handle described herein is also advantageous to the surgeon. The handle mounts the medical instrument that includes the medical tool. The handle also mounts separate control wires for operating the medical tool and for rotating the medical tool and the inner shaft to which the tool is mounted. In one embodiment, which is not intended to be limiting, a first control wire for operating the medical tool is connected to a trigger. The surgeon operates the medical tool, e.g., a forceps or a grasper, by pulling or releasing the trigger and thus closing or opening the forceps of the grasper. The surgeon operates the trigger by means of an orifice for a finger of the surgeon. The handle also includes a mount for a second control feature, a thumbwheel. The thumbwheel may be rotated forwards or backwards, thus advancing or retracting a second control wire used to rotate the inner shaft of the medical instrument and the tool mounted atop the inner shaft. Thus, the surgeon is easily able to control the medical instrument and medical tool with an easy-to-operate handle.

The rotating medical instrument and medical tool may be used with other handles as well. In addition, the devices according to this disclosure are not limited to trigger or thumbwheel control devices. Other controls devices may also be used to control the control wires or control rods that operate or rotate the medical tool.

The handle also includes a device to control tension on the wire that rotates the medical tool, the second control wire. The tension control device is primarily intended to compensate for stretching of the control wire for rotation during use of the rotating medical tool in surgical procedures. The tension control device includes a first reel for reeling wire out and a second reel, a take-up reel. There are a plurality of guide spools for guiding the wire from reel-out to take-up, including spools to guide the wire to and from a pressure sensor and to and from the medical instrument and the medical tool mount of the medical tool. The wire causes rotation of the medical instrument to which the medical tool is attached, and the wire is not directly connected to the medical tool itself. Another control wire, for example a wire to control the opening and closing of a forceps, may be directed connected to the medical tool.

The reel-out and take up reels are mounted on a shaft that also mounts the control thumbwheel. Under normal conditions, the wire will reel out on one side of the wire device, from an un-wind reel or spool and will be taken up by the reel on the opposite side, the re-wind or take-up reel or spool. When the wire stretches, however, there may be additional or excess wire between the reels, i.e., slack. The disclosure includes a pressure sensor to measure the pressure exerted by the wire, an indirect measure of the tension on the wire. If there is slack, the tension and the resulting pressure will be low. If there is tension, the resulting pressure may be higher.

In one embodiment, in order to compensate for stretching of the wire, the tension control device provides a small stepper motor with tension rollers mounted fixedly to the motor or to an assembly that includes the motor. The motor is mounted to a motor mount which holds and guides the motor. Activation of the motor causes the shaft of the motor to rotate in a first direction and move with respect to its position in the motor mount. The motor in its mount, along with the tension rollers, will move to adjust tension on the wire. When tension is low and there is slack in the control wire, the motor and the rollers will move in a first direction, thus moving the motor and the guide rollers in the first direction to increase the tension. In this embodiment, the entire assembly of the motor and two guide rollers moves as a whole. If tension is high, the motor can move in the opposite direction to decrease the tension. The motor thus "floats" between two position extremes. In this embodiment, the path length of the wire from un-wind to re-wind is fixed. Moving the motor and spools in a first direction acts to increase or decrease the path length on one side of the wire while simultaneously decreasing or increasing the path length on the other side. This has the effect of locally increasing or decreasing the tension in those areas, until the wire is further wound or unwound, by the surgeon operating the device.

In a second embodiment, the path length of the wire is actually increased or decreased by the tension control mechanism, thus decreasing or increasing the tension in the entire un-spooled length of the control wire. In this embodiment, the motor is in a fixed position and does not move. The motor has a shaft with right-hand threads on one side and left-hand threads on the opposite side. When the motor rotates in a first direction, the moveable rollers attached to the shafts move away from the motor. This has the effect of lengthening the path of the wire from un-wind to re-wind and lessens the tension on the wire. If the motor rotates in the opposite direction, the moveable rollers move toward the motor, decreasing the length of the overall path of the wire and increasing the tension. The pressure sensor provides an indirect measure of tension by way of its pressure readings. As noted above, the tension spools may be placed on mounts that move in a track or other mechanism that allows for smooth back-and-forth movement when the motor is activated.

In some embodiments, the disclosure is a medical instrument. The medical instrument includes a flexible outer shaft and a flexible inner shaft including an outer surface having a groove. The medical instrument also includes a sliding jacket adapted to fit and move axially between the flexible outer shaft and the flexible inner shaft, the sliding jacket further having an inner guide pin adapted to fit into the groove, and a first control wire attached to the sliding jacket, wherein axial movement of the control wire and the sliding jacket causes rotation of the flexible inner shaft. The groove may be a helical groove.

In some embodiments, the medical instrument further includes a medical tool mounted to the flexible inner shaft and a second control wire attached to the medical tool for controlling the medical tool. In some embodiments, the medical tool is selected from the group consisting of a forceps, a grasper and a cutting tool. In some embodiments, the medical instrument further includes a control handle attached to the second control wire, the control handle adapted to receive the second control wire and manipulate the second control wire. In some embodiments, the control handle is further attached to the first control wire and further includes a control mechanism adapted to allow a user to advance or retract the first control wire and cause rotation of the flexible inner shaft. In some embodiments, the control handle further includes a tension-control mechanism for spooling out and taking in the first control wire. In some embodiments, the medical tool further comprises at least one echogenic or radiopaque feature. In embodiments, the groove spirals over a part of a full length of the outer surface of the flexible inner shaft. In some embodiments, the spiral groove is a helical groove.

The rotating medical tools and the devices or instruments that mount the tools include many advantages. The tools and the devices may easily be operated by surgeon using existing endoscopes, and multiple rotating forceps or tools may be operated by the same surgeon. As noted above, the medical tools, such as forceps, that may be rotated per this disclosure use the same mechanism, a control wire or rod, to operate the tool. The mechanism used to rotate the medical tool is very simple and primarily involves two additional components, the sliding jacket and the second control wire. These are relatively simple parts that do not require special manufacturing skills. As a result, the freely-rotating, minimally-invasive medical tool and its associated medical device may have reasonable costs when compared to existing devices.

The disclosed rotating medical tools and devices may be handled, treated, counted and sterilized in the same manner as exiting tools. There are additional advantages for the surgeons and their patients. The ability to freely rotate the tool may require significantly less effort to properly place and orient the tool for the desired procedure. Thus, less physician or surgeon effort may be required to operate the freely-rotating tools, allowing the physician or surgeon to better concentrate on the procedure and spend less time worrying about placement of the tool within the patient. Finally, the ability to maneuver the tool may require fewer withdrawals and replacements within a given surgical field for a given procedure. This may cause less irritation and trauma to the patient and require less time for the surgeon to accomplish the procedure. While not directly related to costs, these offer advantages to both the surgeon and the patient.

In some embodiments, the control handle further includes a tension control mechanism for the first control wire, the tension control mechanism having a sensor for measuring tension on the first control wire and a motor for adjusting the tension. In some embodiments, the tension control mechanism includes a stepper motor attached to tension rollers. In some embodiments, the control mechanism further includes a photodetector adapted to detect rotation of a thumbwheel for controlling movement of the first control wire and for interrupting tension adjustment until the photodetector ceases to detect rotation of the thumbwheel. In some embodiments, the outer groove of the flexible inner shaft and the inner guide pin of the sliding jacket constitute a camming mechanism.

In some embodiments, the disclosure reveals a medical instrument. The medical instrument includes a flexible outer shaft, a flexible inner shaft having an outer surface having a groove, a medical tool mounted on the flexible inner shaft and a first control wire attached to the medical tool. The medical instrument also includes a sliding jacket adapted to fit and move axially between the flexible outer shaft and the flexible inner shaft, the sliding jacket further having an inner guide pin adapted fit into the groove on the outer surface of the flexible inner shaft. In addition, there is a second control wire attached to the sliding jacket, wherein axial movement of the first control wire is adapted to operate the medical tool and wherein axial movement of the second control wire is adapted to cause movement of the sliding jacket and to cause rotation of the flexible inner shaft and the medical tool.

In some embodiments, the medical tool includes a forceps, wherein the first control wire is adapted to open and close jaws of the forceps. In some embodiments, the medical instrument further includes a control handle adapted to receive the first and second control wires and allow a user to separately operate the medical tool and rotate the flexible inner shaft and medical tool mounted on the flexible inner shaft. In some embodiments, the control handle further includes a take-up mechanism for the second control wire. In some embodiments, the control handle further includes a tension control mechanism for adjusting a tension on the second control wire. In some embodiments, the control handle further includes a tension control mechanism for adjusting a tension on the second control wire, the tension control mechanism including a stepper motor and tension rollers, wherein the stepper motor controls the tension by adjusting a position of the stepper motor and the tension rollers. In some embodiments, the medical instrument further includes a flexible endoscope for mounting and operating the medical instrument.

In some embodiments, there is a medical device. The medical device includes a flexible outer shaft, a flexible inner shaft including an outer surface having a groove, a forceps mounted on the flexible inner shaft, and a first control wire attached to the forceps for operation of the forceps. The medical device also includes a sliding jacket adapted to fit and move axially between the flexible outer shaft and the flexible inner shaft, the sliding jacket further including an inner guide pin adapted fit into the groove on the outer surface of the flexible inner shaft and a second control wire attached to the sliding jacket, wherein axial movement of the first control wire is adapted to open and close jaws of the forceps and wherein axial movement of the second control wire is adapted to cause movement of the sliding jacket and to cause rotation of the flexible inner shaft and the medical tool.

In some embodiments, the flexible inner shaft of the medical device is adapted to rotate with respect to the flexible outer shaft when the sliding jacket moves axially. In some embodiments, the medical device further includes a control handle for mounting the medical tool and for controlling the tool. In some embodiments, the control handle includes separate control devices for the first and second control wires. In some embodiments, the control handle includes a trigger adapted for opening and closing the forceps and a thumbwheel adapted for advancing and retracting the sliding jacket. In some embodiments, the control handle further includes a tension control mechanism for adjusting a tension on the second control wire.

In some embodiments, the tension control mechanism includes a motor with two spools fixedly mounted to the motor, wherein the motor and the two spools traverses in a first direction to increase tension and in a second direction to decrease tension. In some embodiments, the tension control mechanism includes a motor and two spools, a first spool mounted to the motor with a shaft or a portion of a shaft having left-handed threads, a second spool mounted to the motor with a shaft of a portion of a shaft having right-handed threads, the tension control adapted to control tension by rotating the motor in a first direction to cause the two spools to move inwardly toward the motor and in a second direction to cause the two spools to move outwardly from the motor.

In some embodiments, there is a method for operating a medical instrument. The method includes advancing the medical instrument to a region of interest within a patient, operating a medical tool on a distal end of the medical instrument with a first control wire, and rotating the medical tool with a second control wire using a camming mechanism of the medical instrument.

In some embodiments, the medical tool is mounted on an inner shaft of the medical instrument, and the rotating is accomplished by axial movement of a sliding jacket with an inner pin mounted within an outer groove of the inner shaft. In some embodiments, the medical instrument further includes a flexible outer shaft with an inner groove, and the method further includes preventing rotation of the sliding jacket with respect to the flexible outer shaft. In some embodiments, the step of preventing rotation is accomplished with a guide pin mounted on an outside of the sliding jacket, the guide pin mounted within the inner groove of the flexible outer shaft. In some embodiments, the medical tool is selected from the group consisting of a forceps, a grasper and a cutting tool. In some embodiments, the method requires first placing the medical tool in a flexible endoscope mounted in the patient. In some embodiments, the method also includes automatically adjusting a tension of the second control wire with a motorized tensioning mechanism. In some embodiments, the method may also include tracking a location of the medical tool with at least one radiopaque or echogenic feature of the medical tool.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim 1ncludes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A medical instrument, comprising:
a flexible outer shaft;
a flexible inner shaft including an outer surface having a groove;
a sliding jacket adapted to fit and move axially between the flexible outer shaft and the flexible inner shaft, the sliding jacket further comprising an inner guide pin adapted to fit into the groove; and
a first control wire attached to the sliding jacket,
wherein axial movement of the control wire and the sliding jacket causes rotation of the flexible inner shaft.

2. The medical instrument according to claim 1, further comprising a medical tool mounted to the flexible inner shaft and a second control wire attached to the medical tool for controlling the medical tool.

3. The medical instrument according to claim 2, wherein the medical tool is selected from the group consisting of a forceps, a grasper and a cutting tool.

4. The medical instrument according to claim 2, further comprising a control handle attached to the second control wire, the control handle adapted to receive the second control wire and manipulate the second control wire.

5. The medical instrument according to claim 4, wherein the control handle is further attached to the first control wire and further comprises a control mechanism adapted to allow a user to advance or retract the first control wire and cause rotation of the flexible inner shaft.

6. The medical instrument according to claim 4, wherein the control handle further comprises a tension-control mechanism for spooling out and taking in the first control wire.

7. The medical instrument according to claim 6, further comprising a photodetector adapted to detect rotation of a thumbwheel for controlling movement of the first control wire, the photodetector also adapted to interrupt tension adjustment until the photodetector ceases to detect rotation of the thumbwheel.

8. The medical instrument according to claim 4, wherein the control handle further comprises a tension control mechanism for the first control wire, the tension control mechanism comprising a sensor for measuring tension on the first control wire and a motor for adjusting the tension.

9. The medical instrument according to claim 8, wherein the tension control mechanism comprises a stepper motor attached to tension rollers.

10. The medical instrument according to claim 2, wherein the medical tool further comprises at least one echogenic or radiopaque feature.

11. The medical instrument according to claim 1, wherein the outer groove of the flexible inner shaft and the inner guide pin of the sliding jacket constitute a camming mechanism.

12. The medical instrument according to claim 1, wherein the groove spirals around over a part or full length of the outer surface of the flexible inner shaft.

13. The medical instrument according to claim 12, wherein the spiral groove is a helical groove.

14. A medical instrument, comprising:
a flexible outer shaft;
a flexible inner shaft including an outer surface having a groove;
a medical tool mounted on the flexible inner shaft;
a first control wire attached to the medical tool;
a sliding jacket adapted to fit and move axially between the flexible outer shaft and the flexible inner shaft, the sliding jacket further comprising an inner guide pin adapted to fit into the groove on the outer surface of the flexible inner shaft;
a second control wire attached to the sliding jacket,
wherein axial movement of the first control wire is adapted to operate the medical tool and wherein axial movement of the second control wire is adapted to cause movement of the sliding jacket and to cause rotation of the flexible inner shaft and the medical tool.

15. The medical instrument according to claim 14, wherein the medical tool comprises a forceps, wherein the first control wire is adapted to open and close jaws of the forceps.

16. The medical instrument according to claim 14, further comprising a control handle adapted to receive the first and second control wires and allow a user to separately operate the medical tool and rotate the flexible inner shaft and medical tool mounted on the flexible inner shaft.

17. The medical instrument according to claim 16, wherein the control handle further comprises a take-up mechanism for the second control wire.

18. The medical instrument according to claim 16, wherein the control handle further comprises a tension control mechanism for adjusting a tension on the second control wire.

19. The medical instrument according to claim 16, wherein the control handle further comprises a tension control mechanism for adjusting a tension on the second control wire, the tension control mechanism comprising a stepper motor and tension rollers, wherein the stepper motor controls the tension by adjusting a position of the stepper motor and the tension rollers.

20. The medical instrument according to claim 14, further comprising a flexible endoscope for mounting and operating the medical instrument.

21. A medical instrument, comprising:
a flexible outer shaft;
a flexible inner shaft including an outer surface having a groove;
a forceps mounted on the flexible inner shaft;
a first control wire attached to the forceps for operation of the forceps;
a sliding jacket adapted to fit and move axially between the flexible outer shaft and the flexible inner shaft, the sliding jacket further comprising an inner guide pin adapted to fit into the groove on the outer surface of the flexible inner shaft;
a second control wire attached to the sliding jacket,
wherein axial movement of the first control wire is adapted to open and close jaws of the forceps and wherein axial movement of the second control wire is adapted to cause movement of the sliding jacket and to cause rotation of the flexible inner shaft and the medical tool.

22. The medical instrument according to claim 21, wherein the flexible inner shaft is adapted to rotate with respect to the flexible outer shaft when the sliding jacket moves axially.

23. The medical instrument according to claim 21, further comprising a control handle for mounting the medical tool and for controlling the tool.

24. The medical instrument according to claim 23, wherein the control handle comprises separate control devices for the first and second control wires.

25. The medical instrument according to claim 23, wherein the control handle comprises a trigger adapted for opening and closing the forceps and a thumbwheel adapted for advancing and retracting the sliding jacket.

26. The medical instrument according to claim 23, wherein the control handle further comprises a tension control mechanism for adjusting a tension on the second control wire.

27. The medical instrument according to claim 26, wherein the tension control mechanism comprises a motor with two spools fixedly mounted to the motor, wherein the motor and the two spools travel in a first direction to increase tension and in a second direction to decrease tension.

28. The medical instrument according to claim 26, wherein the tension control mechanism comprises a motor and two spools, a first spool mounted to the motor with a shaft or a portion of a shaft having left-handed threads, a second spool mounted to the motor with a shaft of a portion of a shaft having right-handed threads, the tension control adapted to control tension by rotating the motor in a first direction to cause the two spools to move inwardly toward the motor and in a second direction to cause the two spools to move outwardly from the motor.

29. A method for operating a medical instrument, the method comprising:
mounting a medical tool on an inner shaft of the medical instrument, the medical instrument also comprising a flexible outer shaft with an inner groove;
advancing the medical instrument to a region of interest within a patient;
operating the medical tool on a distal end of the medical instrument with a first control wire; and
rotating the medical tool with a second control wire using a camming mechanism of the medical instrument, wherein the rotating is accomplished by axial movement of a sliding jacket with an inner pin mounted within a groove defined by the inner shaft along an outer surface.

30. The method of claim 29, wherein the groove is a helical groove and wherein rotating is accomplished by axial movement of the sliding jacket with the inner pin mounted within the helical outer groove of the inner shaft.

31. The method of claim 29, further comprising preventing rotation of the sliding jacket with respect to the flexible outer shaft.

32. The method of claim 31, wherein the step of preventing rotation is accomplished with a guide pin mounted on an outside of the sliding jacket, the guide pin mounted within the inner groove of the flexible outer shaft.

33. The method of claim 29, wherein the medical tool is selected from the group consisting of a forceps, a grasper and a cutting tool.

34. The method of claim 29, further comprising first placing the medical tool in a flexible endoscope mounted in the patient.

35. The method of claim 29, further comprising automatically adjusting a tension of the second control wire with a motorized tensioning mechanism.

36. The method of claim 29, further comprising tracking a location of the medical tool with at least one radiopaque or echogenic feature of the medical tool.

* * * * *